United States Patent (12)
Lim et al.

(10) Patent No.: US 6,469,209 B1
(45) Date of Patent: Oct. 22, 2002

(54) ACRYLATE-TYPE FUNGICIDE

(75) Inventors: Hong Lim, Seoul (KR); Bong Jin Chung, Anyang-si (KR); Jong Sang Chung, Daejeon-si (KR); In Young Choi, Daejeon-si (KR); Dae Jong Park, Daejeon-si (KR); Chang Il Hwang, Daejeon-si (KR)

(73) Assignee: Dongbu Hannong Chemical Co., Ltd. (KR)

( * ) Notice: Subject to any disclaimer, the term of this patent is extended or adjusted under 35 U.S.C. 154(b) by 0 days.

(21) Appl. No.: 10/009,701
(22) PCT Filed: Jul. 4, 2000
(86) PCT No.: PCT/KR00/00716
§ 371 (c)(1),
(2), (4) Date: Dec. 14, 2001
(87) PCT Pub. No.: WO01/01779
PCT Pub. Date: Jan. 11, 2001

(30) Foreign Application Priority Data

Jul. 5, 1999 (KR) ............................................. 99-26946

(51) Int. Cl.[7] ..................... C07C 233/09; C07C 231/02; A01N 37/18
(52) U.S. Cl. ....................... 564/164; 564/134; 564/163; 564/165; 514/619; 514/620
(58) Field of Search ................................. 564/163, 164, 564/165, 134; 514/619, 620

(56) References Cited

U.S. PATENT DOCUMENTS 5,627,284 A 5/1997 Takase et al.
6,369,090 B1 * 4/2002 Schelberger et al. ........ 514/384

FOREIGN PATENT DOCUMENTS

EP 0 623 604 A2 4/1994
EP 0 628 540 A1 5/1994
WO WO 96/17851 6/1996

OTHER PUBLICATIONS

International Preliminary Examination Report No. PCT/KR00/00716 Dated: Feb. 6, 2002.

* cited by examiner

Primary Examiner—Shailendra Kumar
(74) Attorney, Agent, or Firm—Roberts & Merchanti, LLP.

(57) ABSTRACT

The present invention relates to novel acrylate-type N-methyl E-2-(2-methylphenyl)oxymethyl)-6-methylphenyl-glyoxylamide O-methyl oxime represented by formula (1), its preparation method and its use as fungicides. The compound of the present invention has not only stronger fungicidal effect on plant pathogens at low concentrations but also broader fungicidal spectrum than the conventional fungicides. Especially, because the compound has excellent systemic and curative effect as well as no toxicity, it can be used as an efficacious agricultural fungicide. In addition, the compound of the present invention can be useful as environmental-friendly fungicide capable of causing less environmental pollution fungicide due to its strong fungicidal effect at low concentrations.

14 Claims, No Drawings

ACRYLATE-TYPE FUNGICIDE

This patent application claims a benefit of priority from Korean Patent Application No. 1999/26946 filed Jul. 5, 1999, through PCT Application Serial No. PCT/KR00/00716 filed Jul. 4, 2000, the contents of each of which are incorporated herein by reference.

FIELD OF THE INVENTION

The present invention relates to novel acrylate-type N-methyl E-2-((2-methylphenyl)oxymethyl)-6-methylphenylglyoxyl amide O-methyl oxime represented by the following formula 1, its preparation method and its use as fungicides. The compound of the present invention has not only stronger fungicidal effect on plant pathogens at low concentrations but also broader fungicidal spectrum than the conventional fungicides. Especially, because the compound has excellent systemic and curative effect as well as no toxicity, it can be used an efficacious agricultural fungicide. In addition, the compound of the present invention can be useful as environmental-friendly fungicide capable of causing less environmental pollution fungicide due to its strong fungicidal effect at low concentrations.

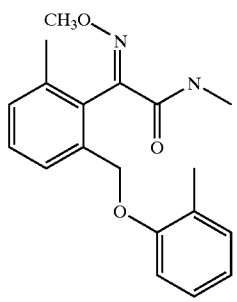

Formula 1

BACKGROUND

In spite of their strong fungicidal effect, agricultural fungicides currently in use have been a source of problems, because the required amount is ever increasing as tolerance of target plant pathogens increases. Thus, there is a need to develop new fungicides with strong fungicidal effect and broad fungicidal spectrum. Acrylate-type compounds have been developed as an environment-friendly alternative to the conventional fungicides.

The acrylate fungicides currently in use have strong fungicidal effect on pathogenic fungi of plant origin with broad fungicidal spectrum [EP patent No.: 382, 375 (ICIA5504), U.S. Pat. No. : 4,829,085 (BAS490F), EP patent No.: 398,692 (SSE-126)]. There have been continuing developments of more effective acrylate fungicides.

Among those recently developed, alkoxyiminoaceteamide derivatives with two aryl groups and an ether linkage, have been shown to have strong fungicidal effect on pathogenic fungi at low concentrations with broad fungicidal spectrum. The conventional techniques of their use are described in international publication No.: WO 9617851 and WO 9534526, German publication No.: DE 4312637 and DE 4030038, and European publication No.: EP 398692. The inventors of the present invention also had applied for a patent on alkoxyiminoaceteamide derivative compounds (Korean patent application No.: 98-21068)

The inventors of the present invention developed novel acrylate-type N-methyl E-2-((2-methylphenyl)oxymethyl)-6-methylphenylglyoxylamide O-methyl oxime with outstanding fungicidal effect at low concentrations with broad fungicidal spectrum, especially the compound is superior to the conventional fungicides in terms of systemic as well as curative effect.

SUMMARY OF THE INVENTION

It is an object of this invention to provide novel acrylate-type N-methyl E-2-((2-methylphenyl)oxymethyl)-6-methylphenylglyoxylamide O-methyl oxime represented by the formula 1.

It is a further object of this invention to provide a method for preparing novel acrylate-type N-methyl E-2-((2-methylphenyl)oxymethyl)-6-methylphenylglyoxylamide O-methyl oxime.

It is an additional object of this invention to provide agricultural fungicides, containing acrylate-type N-methyl E-2-((2-methylphenyl)oxymethyl)-6-methylphenylglyoxylamide O-methyl oxime as an active ingredient.

DETAILED DESCRIPTION OF PREFERRED EMBODIMENTS

Hereinafter, the present invention is described in detail.

The present invention provides novel acrylate-type N-methyl E-2-((2-methylphenyl) oxymethyl)-6-methylphenylglyoxyl amide O-methyl oxime represented by the formula 1.

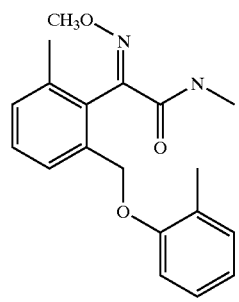

Formula 1

The acrylate-type compound represented by the formula 1 of the present invention, namely N-methyl E-2-((2-methylphenyl)oxymethyl)-6-methylphenylglyoxylamide O-methyl oxime, shows broad fungicidal spectrum as well as strong fungicidal effect on plant pathogens at low concentrations. The compound also has excellent curative effect and remarkable systemic effect in plant body.

The compound of the present invention is especially superior to the conventional fungicides such as triazole-type flusilazole or acrylate-type kresoxim methyl (BAS490F) in the protection from barley powder mildew and wheat leaf rust at low concentrations. In addition, the compound of the present invention shows remarkable control efficacy on rice blast, tomato late blight and rice sheath blight at low concentrations. Thus, the compound has been shown to be remarkably effective on various kinds of plant pathogens.

The present invention provides a method of preparation for the novel acrylate-type N-methyl E-2-((2-methylphenyl) oxymethyl)-6-methylphenylglyoxylamide O-methyl oxime represented by the formula 1.

The method for preparing the compound according to the present invention is summarized in the following steps.

1) methyl E-2-bromomethyl-6-methylphenylglyoxylate O-methyl oxime is reacted with o-cresol under a basic condition to give methyl E-2-((2-methylphenyl)oxymethyl)-6-methylphenylglyoxylate O-methyl oxime (step 1); and 2) methyl E-2-((2-methylphenyl)oxymethyl)-6-methylphenylglyoxylate O-methyl oxime prepared in the step 1 is reacted with methylamine (NH₂Me) to give N-methyl E-2-((2-methylphenyl)oxymethyl)-6-methylphenylglyoxylamide O-methyl oxime of the present invention (step 2).

The preparation of methyl E-2-((2-methylphenyl)oxymethyl)-6-methylphenylglyoxylate O-methyl oxime (formula 2) of the step 1 may be done as in the scheme 1.

Scheme 1

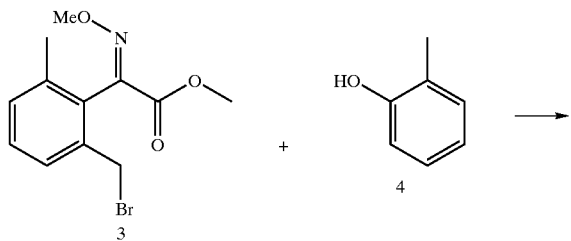

Methyl E-2-bromomethyl-6-methylphenylglyoxylate O-methyl oxime of the formula 3 is reacted with o-cresol of the formula 4 under an appropriate basic condition to give the compound of the formula 2. The base may be preferably selected from the group comprising K₂CO₃, Na₂CO₃, triethylamine (TEA) and sodium hydride (NaH), etc. A variety of reaction solvents including dimethylformamide (DMF), tetrahydrofuran (THF), chloroform (CHC₃) and etc. may be used. The reaction temperature may be −20~100° C., preferably −10~30° C.

Methyl alkoxyiminoacetate of the formula 2 prepared in the scheme 1 is reacted with methylamine to give N-methyl E-2-((2-methylphenyl)oxymethyl)-6-methylphenylglyoxylamide O-methyl oxime of the formula 1 as represented in the scheme 2.

Scheme 2

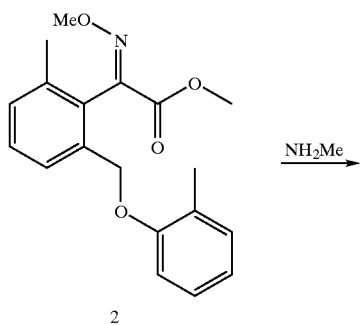

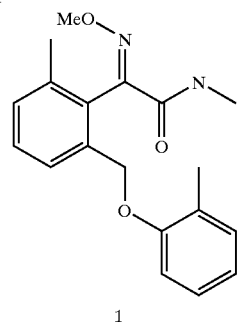

In the above reaction, the number of equivalent of methylamine may be 1–10, preferably 5. The reaction solvents are preferably used dimethylforamide (DMF), tetrahydrofuran (THF), chloroform (CHCl₃), etc. The reaction temperature may be 0~100° C., preferably 0~30° C.

Methyl E-2-bromomethyl-6-methylphenylglyoxylate O-methyl oxime (formula 3), the reactant of the scheme 1, can be prepared by the method in the scheme 3.

Scheme 3

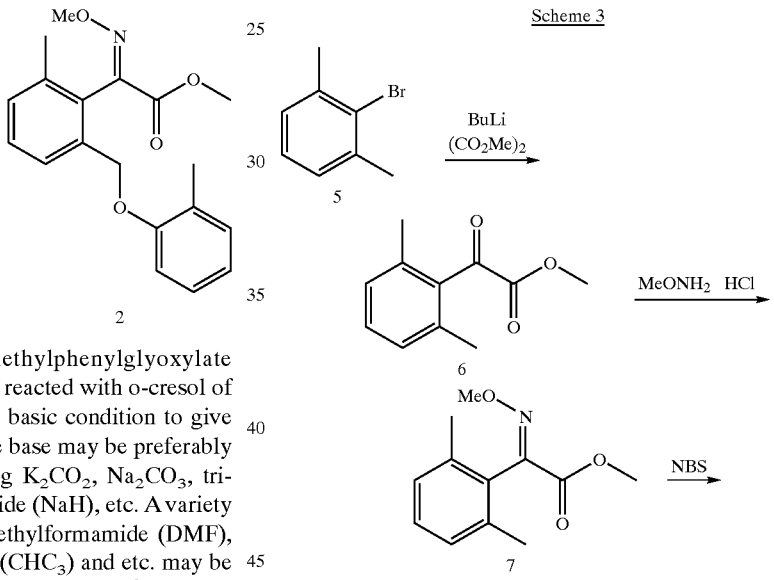

Methyl 2,6-dimethylphenylglyoxylate of the formula 6 is obtained by the reaction of 2-bromo-m-xylene of the formula 5 with buthyllithium (BuLi), followed by the reaction with dimethyl oxalate [(CO₂Me)₂]. The compound of the formula 6 is reacted with methoxylamine hydrochloride (MeONH₂.HCl) to give methyl E-2,6-dimethylphenylglyoxylate O-methyl oxime of the formula 7 [U.S. Pat. No. : 5,371,223 (1994)]. The compound of the formula 7 is reacted with N-bromosuccinimide (NBS) to give the compound of the formula 3 [U.S. Pat. No. : 5,371,223 (1994); L. Horner Angew. Chem. 71 (1959), 349].

The present invention also provides agricultural fungicides, containing N-methyl E-2-((2-methylphenyl) oxymethyl)-6-methylphenylglyoxylamide O-methyl oxime as an active ingredient.

N-Methyl E-2-((2-methylphenyl)oxymethyl)-6-methylphenyl glyoxylamide O-methyl oxime of the present invention can be a useful agricultural fungicides due to its strong fungicidal effect at low concentrations, broad fungicidal spectrum, especially, excellent curative and systemic effect, and no phytotoxicity.

Agricultural fungicides can be formulated as a single compound of the formula 1, or as a mixture with other compounds to improve the fungicidal effect and to broaden the spectrum of target pathogens.

The compound of the present invention can be used to control and reduce damage in the case of the followings: crops such as rice, wheat, barley, etc.; fruits such as an apple, a pear, an orange, a grape, a banana, a peach, etc.; coffee; tea; vegetables such as a potato, a red pepper, a pimento, a tomato, a cucumber, a watermelon, a melon, a lettuce, a Chinese cabbage, a celery, a rape, a peanut, a cabbage, a green onion, a garlic, a ginger, an onion; a grass; seeding trees for gardens and forestry; and flowers such as a carnation, a lily, a rose, a chrysanthemum, etc. It may also be used for seeds and agricultural products during storage.

The compound of the present invention can be used to control the disease caused by the phytopathogen classified as according to the pathogenic taxonomy in the following genus and species: *Pyricularia oryzae, Rhizoctonia solani, Puccinia recondita, Puccinia striiformis, Erysiphe graminis, Sphaerotheca fuliginea, Sphaerotheca macularis*, Elsinoe spp., *Podosphaera leucotricha, Uncinula necator*, Helminthosporium spp., Alternaria spp., Rhynchosporium spp., Septoria spp., Pyrenophora spp., *Botryosphaeria dothidea, Pseudocercosporella herpotrichoides, Gaeumannomyces graminis*, Cercospora spp., *Cercosporidium personata, Botrytis cinerea, Venturia inaequalis*, Cladosporium spp., *Plasmopara viticola, Bremia lactucae*, Peronospora spp., *Pseudocercospora humuli, Pseudoperonospora cubensis, Phytophthora infestans, Phytophthora capsici*, Phytophthora spp., Penicillium spp., *Trichoderma viride, Gloeosporium musarum, Glomerella cingulata, Mycosphaerella melonis*, Fusarium spp., and *Marssonina mali*.

In particular, the compound of the present invention has excellent fungicidal effect on barley powdery mildew and wheat leaf rust, rice blast, rice sheath blight, cucumber gray mould and tomato late blight, etc.

In addition, the fungicidal compositions of the present invention can be employed in combination with one or more additional known pesticides such as fungicides, plant growth regulators, insecticides and herbicides, and if necessary, fertilizers, in suitable ratio, in order to improve the fungicidal effect or to broaden the spectrum of target pathogen. Such additional pesticides are followed:

1) fungicides—aldimorph, anilazine, BAS490F, benalaxyl, benomyl, biloxazol, binapacryl, bitertanol, blasticidin S, bromuconazole, bupirimate, buthiobate, captafol, captan, carbendazim, carboxin, chlorothalonil, copper oxychloride, copper sulphate, cycloheximide, cymoxanil, cyproconazole, dichlofluanide, dichlone, diclomezin, dicloran, difenoconazole, dimethomorph, diniconazole, dinocap, dithianon, dodemorph, edifenphos, etaconazole, ethirimol, etridiazole, fenarimol, fenpiclonil, fenpropidin, fenpropimorph, fentin acetate, flutolanil, flutriafol, flusilazole, folpet, fosetyl-aluminium, furalaxyl, guazatin, hexaconazole, hydroxyisoxazole, ICIA5504, imazalil, imibenconazole, iprobenfos, iprodione, isoprothiolane, kasugamycin, mancozeb, maneb, mepanipyrim, mepronil, metalaxyl, methfuroxam, myclobutanil, neoasozin, nuarimol, ofurace, oxadixyl, oxycarboxin, pefurazoate, penconazole, pencycuron, phenazin oxide, phthalide, polyoxinD, polyram, probenazole, prochloraz, procymidone, propamocarb, propiconazole, propineb, prothiocarb, pyrazophos, pyrifenox, pyrrolnitrin, quintozene, SSF-109, SSF-126, streptomycin, tebuconazole, tetraconazole, thiabendazole, thicyofen, thiophanate-methyl, thiram, tolclofos-methyl, triacetate salt of 1,1-iminodi(octamethylene)diguanidine, triadimefon, triadimenol, tricyclazole, tecnazene, tridemorph, triforine, validamycin A, vinclozolin, zarilamid, and zineb;

2) insecticides—acetamiprid, buprofezin, carbaryl, carbofuran, carbosulfan, chlopyrifos, cyclopyrothrin, demeton-s-methyl, diazinon, dimethoate, ethofenprox, fenitrothion, fenobucarb, fenthion, fipronil, furathiocarb, imidacloprid, isoprocarb, isoxathion, monocrotophos, phenthoate, pirimicarb, and propaphos;

3) plant growth regulators and herbicides—3,6-dichloropicolinic acid, 1-(4-chlorophenyl)-4,6-dimethyl-2-oxo-1,2-dihydropyridine-3-carboxylic acid, methyl-3,6-dichloroanisate, abscisic acid, asulam, benzoylprop-ethyl, carbetamide, daminozide, difenzoquat, dikegulac, ethephon, fenpentezol, fluoridamid, glyphosate, glyphosine, hydroxy-benzonitriles (i.e. bromoxynil), inabenfide, isopyrimol, long chain fatty alcohols and acids, maleic hydrazide, mefluidide, morphactins (i.e. chlorfluoroecol), paclobutrazol, phenoxy-acetic acids (i.e. 2,4-D or MCPA), substituted benzoic acid (i.e. triiodobenzoic acid), substituted quaternary ammonium and phosphonium compounds (i.e. chloromequat, chlorphonium or mepiquatchloride), tecnazene, auxins (i.e. indoleacetic acid, indolebutyric acid, and naphthoxyacetic acid), cytokinins (i.e. benzimidazole, benzyladenine, benzyladenopurine, diphenylurea, and kinetin), gibberellins (i.e. GA3, GA4 and GA7), and triapenthenol.

Although the compound of the Dresent invention can be used directly on the plants, it is used mostly in the form of formulations for convenience and stability. The type of formulations may vary depending on the purpose.

The fungicides containing the compound of the present invention can be formulated in forms of wettable powders, emulsifiable concentrates, granules, dustable powders, suspension concentrates, water dispersible granules, up-granules and wettable powders for seed treatment and pastes. The fungicides containing the compound of the present invention as an active compound, can be applied (sprayed or painted) directly to leaves, trunks, branches, roots or seeds of plants including crops, seedlings, shrubs and trees, or in the mixture with a general soil and a seedling culture soil or culture medium for planting of a paddy or a upland field. It may also be used to treat aquiculture medium for the control of phytopathogens.

The fungicidal compositions are preferred to comprise one or more active compounds of the present invention with solid or liquid carriers and various inert ingredients to improve the adhesion and stability of the compounds of the present invention, an active ingredient, and to attain user's convenience. At this time, the compositions ratio of the compounds according to the present invention is preferred to be 1–90 wt % in the case of wettable powders, emulsifiable concentrates, and wettable powders or suspension concentrates for seed treatment, 0.1–10 wt % in the case of dustable powders, 1–50 wt % in the case of suspension concentrates, 1–30 wt % in the case of granules or up-granules, and less than 25 wt % in the case of a mixture or dressing with fertilizers (i.e. fertilizers containing nitrogen, phosphorus and potassium), and the compositions ratio is variable according to the purposed use of the compositions.

In the formulation for the compound of the present invention as the carriers, the preferred liquid carriers are water, alcohols (i.e. methanol, benzyl alcohol, furfuryl alcohol, butanol, ethylene glycol, glycerin, etc.), ketones (i.e. cyclohexanone, acetone, methylethyl ketone, etc.), ethers (i.e. dioxane, tetrahydrofuran, celosolb, etc.), aliphatic hydrocarbons (i.e. gasoline, kerosene, etc.), halogenated hydrocarbons (i.e. chloroform, carbon tetrachloride, etc.), acid amides (i.e. dimethylformamide, etc.), esters (i.e. ethyl acetate, butyl acetate, ethylene glycol acetate, aliphatic acid glycerin ester, etc.), nitrites (i.e. acetonitrile, etc.) and aromatic hydrocarbons (i.e. benzene, toluene, xylene, etc.). The said carriers can be used as a single or mixture. And the preferred solid carriers are mineral fillers (i.e. kaolin, clay, bentonite, acidic white clay, talc, silica, sand, diatom earth, dolomite, calcium carbonate, powdery magnesium, gypsum, etc.) and vegetable powders (i.e. soybean flour, wheat flour, sawdust, starch flour, crystalline cellulose, etc.).

In addition, the fungicidal compositions of the present invention may include emulsifiers, binders, dispersants, penetrants, and surfactants of anionic, cationic or nonionic type. The cationic surfactants may be long-chained alkyl ammonium salt such as bromo cetyltrimethylammonium salt. The anionic surfactants include alkali metal salts, alkali earth metal salts or ammonium salts of the following compounds: alkylarylsulfonic acid such as dodecylbenzenesulfonic acid; alkyloxysulfonic acid such as lauryloxysulfonic acid; arylsulfonic acids such as ligninsulfonic acid, naphthalenesulfonic acid and dibutyl naphthalenesulfonic acid; laurylether sulfate; aliphatic alcohol sulfate; aliphatic acid; hexadecanol sulfate; heptandecanol sulfate; and glycol ether. The nonionic surfactants include aliphatic alcohols such as oleyl alcohol and cetyl alcohol, caster oil containing phenol, alkyl phenol, ethylene oxide, propylene oxide, and the condensation product of naphthalenesulfonic acid with either phenol or formaldehyde.

The fungicidal compositions for seed treatment may include binders to improve the adhesion, and use N-methylpyrrolidine, propylene glycol or N,N-dimethylformamide as a solvent.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Preparation 1

Preparation of Methyl E-2-Bromomethyl-6-Methylphenylglyoxylate O-methyl Oxime (Formula 3)

(Step 1) Preparation of Methyl 2.6-Dimethylglyoxylate (Formula 6)

Buthyllithium (2.5 M in hexane, 78 mL, 0.19 mol) was added in THF (150 mL) at −78° C. To this solution was added dropwise 2-bromo-m-xylene (30 g, 0.16 mol) and the reaction mixture was stirred for 2 hours at the same temperature. To the solution of dimethyloxalate (38 g, 0.32 mol) in THF (600 mL) was added dropwise the lithuated solution at −78° C. After stirred for 3 hours, the reaction mixture was quenched with aqueous ammonium chloride solution and allowed to warm to room temperature. The mixture was added with water (500 mL), extracted with ether (200 mL) three times. The combined organic layers were dried over anhydrous magnesium sulfate and concentrated in vacuo. The residue was solidified with hexane and filtered. The filtrate was concentrated to give the product (24.3 g, 79%) which was used in the next reaction without further purification:

$^1$H NMR (CDCl$_3$); δ2.29 (s, 6H), 3.92 (s, 3H), 7.08 (d, 2H, J=7.7 Hz), 7.28 (t, 1H, J=7.9 Hz).

(Step 2) Preparation of Methyl E-2.6-Dimethylphenylgly-Oxylate O-methyl Oxime (Formula 7)

A mixture of methyl 2,6-dimethylphenylglyoxylate (24.3 g, 0.126 mol) and methoxylamine hydrochloride (12 g, 0.14 mol) in methanol (150 mL) was refluxed for 3 hours. After the solvent was removed in vacuo, the residue was added with water (150 mL) and extracted with ethyl acetate (100 mL) twice. The combined organic layers were dried over anhydrous magnesium sulfate and concentrated in vacuo. The resultant was recrystallized with hexane to give the product (12 g, 43%):

$_1$H NMR (CDCl$_3$); δ2.17 (s,3H), 3.89 (s, 3H), 4.07 (s, 3H), 7.06~7.26 (m, 3H).

(Step 3) Preparation of Methyl E-2-Bromomethyl-6-Methylphenylglyoxylate O-Methyl Oxime (Formula 3)

A mixture of N-bromosuccinimide (11 g, 0.596 mol), 2,2-azobisisobutyronitrile (89 mg, 0.540 mol) and methyl E-2,6-dimethylphenylglyoxylate O-methyl oxime (12 g, 0.542 mol) in CCl$_4$ (200 mL) was refluxed for 4 hours under 300 W lamp. The cooled reaction mixture was filtered, concentrated in vacuo to give the product (17.2 g, 100%) which was used in the next reaction without further purification:

$^1$H NMR (CDCl$_3$); δ2.19 (s, 3H), 3.89 (s, 3H), 4.09 (s, 3H), 4.32 (s, 2H), 7.27~7.50 (m, 3H).

Preparation 2

Preparation of Methyl E-2-((2-Methyl Phenyl) Oxymethyl)-6-Methylphenylglyoxylate O-Methyl Oxime (Formula 2).

o-Cresol (5.9 g, 0.542 mol) was added to a suspension solution of sodium hydride (95%, 2 g, 0.813 mol) in DMF (100 mL) at 0 ° C., the reaction mixture was stirred for 1 hour at room temperature. This above reaction solution was added dropwise to a solution of methyl E-2-bromomethyl-6-methylphenylglyoxylate O-methyl oxime (16.2 g, 0.542 mol) in DMF (100 mL) for 30 min at 0 ° C. After was stirred for 1 hour at room temperature, the reaction mixture was added water (200 mL) and extracted with ether (100 mL) three times. The combined organic layers were washed with water, dried over anhydrous magnesium sulfate and concentrated in vacuo to give the crude product which was used in the next reaction without further purification.

Example 1: Preparation of N-methyl E-2-((2-Methylphenyl)Oxymethyl)-6-Methylglyoxylamide O-methyl Oxime (Formula 1)

Methylamine (40% in methanol, 11 g, 0.137 mol) was added dropwise to a solution of methyl E-2-((2-methylphenyl) oxymethyl)-6-methylphenylglyoxylate O-methyl oxime (9 g, 0.274 mol) in THF (50 mL) and the reaction mixture was stirred for 3 hours at room temperature. The solvent was removed in vacuo and the residue was purified by chromatography on silica gel (ethyl acetate:hexane=1:2) to give the product (6 g, 67%):

$^1$H NMR (CDCl$_3$); δ2.21 (s, 3H), 2.26 (s, 3H), 2.91 (d, 3H, J=5.1 Hz), 3.97 (s, 3H), 4.90 (dd, 2H, J=12.3 Hz), 6.68 (bs, 1H), 6.79~6.91 (m, 2H), 7.08~7.41 (m, 5H).

The following examples illustrate the agricultural fungicidal compositions which can be prepared from the compound of the formula 1 of the present invention.
<Formulation 1>Wettable Powder

| The compound of the formula 1 | 10% |
|---|---|
| NK250L (surfactant) | 10% |
| White carbon | 10% |
| Pyrophylite (carriers) | 70% |

Wettable powder was prepared by mixing all the components, followed by pulverization.
<Formulation 2>Emulsifiable Concentrate

| The compound of the formula 1 | 10% |
|---|---|
| DDY2000 (surfactant) | 10% |
| Xylene | 80% |

Emulsifiable concentrate was prepared by mixing all the components, followed by pulverization.
<Formulation 3>Suspension Concentrate

| The compound of the formula 1 | 10% |
|---|---|
| HY1910 (surfactant) | 10% |
| Propylene glycol | 5% |
| Zantan gum | 0.2% |
| KM-73(defoamer) | 0.15% |
| Biocide-LS (antiseptics) | 0.2% |
| KNP (dispersants) | 0.1% |
| Water (carriers) | 74.35% |

Suspension concentrate was prepared by mixing all the components, followed by pulverization in ball mill.
<Formulation 4>Up-granule

| The compound of the formula 1 | 5% |
|---|---|
| Paraffin oil | 7.5% |
| Sodium alkalsulfosuccinate (surfactant) | 2% |
| White carbon | 3% |
| Zantan gum | 1.2% |
| Sodium polyacrylacid | 0.8% |
| Potassium chloride | 80.5% |

Up-granule was prepared by mixing all the components, followed by granulation and drying with horisontal extruder.
<Formulation 5>Granule

| The compound of the formula 1 | 5% |
|---|---|
| HY1910 (surfactant) | 2.5% |
| NY250L (surfactant) | 0.2% |
| Soda ash | 0.5% |
| Dextrin | 2.0% |
| Bentonite | 25% |
| Talc | 64.8% |

Granule was prepared by mixing all the components with water, followed by granulation and drying with horisontal extruder.

Experiment 1

Protective Effect Test I

In order to examine the control efficacy of N-methyl E-2-((2-methylphenyl)oxymethyl)-6-methylphenylglyoxylamide O-methyl oxime represented by formula 1 of the present invention on various plant pathogens, the present inventors performed the following experiments.

To examine protective effect of the above agricultural fungicidal compositions on plant pathogens, the compound of the present invention was dissolved in acetone solution (10%). To the acetone solution (10%), Tween-21 was added at the concentration of 500 ppm for rice and 250 ppm for the others. The resulting solution (50 mL) was sprayed on plants. Wettable powders of tricyclazole, procymidone, dimethomorph and flusilazole, soluble concentrate of validamycin, and kresoxim methyl (BAS490F) were used as controls.

Plants sprayed with the agricultural fungicidal compositions were left at room temperature for 24 hours to volatilize solvents and water, and inoculated with the pathogens prepared as follows. Control efficacy of the agricultural fungicidal compositions was tested on rice blast, rice sheath blight, cucumber gray mould, tomato late blight, wheat leaf rust and barley powdery mildew. All the experiments were repeated three times. When control efficacy was 100% at the concentration of first test for the agricultural fungicidal compositions, the test was performed at the gradually decreased concentrations.

Control value of each compound was calculated by the following mathematical formula 1.
<Mathematical formula 1>

Control value(%)=(1—a ratio of the diseased areas in treated leaves/a ratio of the diseased areas in untreated leaves)×100

1) Protective Effect Test on Rice Blast (RCB)

A plant pathogen, *Pyricularia oryzae* Cavara KJ301 strain, was inoculated on rice bran agar medium (rice bran 20 g, dextrose 10 g, agar 15 g, distilled water 1 L) and incubated at 26° C. for 2 weeks in a growth chamber. The aerial mycelium was removed by scratching the medium surface on which the pathogen grew, using a rubber polishman, and incubated at 25–28° C. for 48 hours in a shelf illuminated by the fluorescent light to form spores. The conidiospore formed was harvested and suspended in sterile water to the concentration of 10 spores/mL. Rice plants ('Nakdong-Byeo') in 3 or 4-leaf stage sensitive to rice blast, were inoculated by spraying the suspension solution of conidiospores, and incubated at 26 C and 100% relative humidity for 24 hours in a dark chamber to infiltrate the pathogen. The above rice plants were incubated at 26±2° C. and 80% relative humidity for 5 days in the growth chamber to induce the rice blast. The ratio of diseased area formed on the completely open leaves positioned under the apical leaf at 3 or 4-leaf stage was examined.

2) Protective Effect Test on Rice Sheath Blight (RSB)

After a plant pathogen, *Rhizoctonia solani* AG-1, was inoculated on Lhe PDA (Potato-Dextrose Agar) medium, agar disk containing pathogenic mycelium was inoculated on the growth medium prepared by sterilizing the appropriate amount of wheat bran in a 1 L-culturing bottle, and incubated at 27±1° C. for 7 days in a growth chamber. For inoculating the plant pathogen, the pellet of mycelium cultured on the growth medium was finely ground and inoculated uniformly on the ground surface of rice plants ('Nakdong-Byeo') at 2 or 3 leaf-stage in a small pot (diameter 5 cm). After the pathogenic-inoculated rice plants were incubated at 28±1° C. for 1 day in a dew chamber, they were incubated at 29±1° C. and more than 85% relative humidity for 5 days in a growth chamber to induce the rice sheath blight. The diseased area of leaves was measured to examine the induction of the disease, and the ratio of the diseased sheath areas to total sheath areas of the young seedlings of rice at 2 or 3-leaf stage was examined.

3) Protective Effect Test on Cucumber Gray Mould (CGM)

A plant pathogen, *Botrytis cinerea*, was inoculated on the petri dish containing PDA medium and incubated at 20±1° C. for 10 days in a growth chamber illuminated by a fluorescent light to induce conidiospore as inoculum. After sterile PD broth was poured into the above petri dish, the conidiospore was harvested with a sterilized brush and used as inoculum. Young seedling of cucumber (house Baekdadagi® cucumber) was sowed in a small pot (diameter 6.5 cm), and grown and tested until its true leaves were completely open. A suspension solution of the pathogen conidiospore (PD broth+the pathogen conidiospore) as inoculum were sprayed on leaves of the cucumber. The inoculated cucumbers were incubated at 20±1° C. and 100% relative humidity for 5 days in a dew chamber to induce cucumber gray mould. The diseased areas of the induced cucumber leaves was measured to examine a degree of the disease induction, and then a ratio of the diseased areas to total areas in first true leaves of cucumber was examined.

4) Protective Effect Test on Tomato Late Blight (TLB)

A plant pathogen causing tomato late blight, *Phytophthora infestans*, was inoculated on the petri dish containing a sterilized V-8 juice agar, and incubated at 20±1° C. for 7 days in a growth chamber, which was illuminated by a fluorescent light to form zoosporangium required for inoculation. After pouring the sterile water into the petri dish that zoosporangium was formed on, the zoosporangium was harvested with a sterilized brush, and incubated at 4° C. in refrigerator to release zoospores. The zoospores were adjusted to the concentration of $10^6$ spores/ml, and used as inoculum. Tomato seeds was sowed in a small pot (diameter 6.5 cm), grown for 2 weeks and used for the test. The suspension solution of zoospore were uniformly sprayed on the open tomato leaves. Immediately after inoculation, the young seedlings of the tomato were incubated at 20° C. and 100% relative humidity for 6 days in a dew chamber to induce the tomato late blight. A ratio of the diseased areas to the total areas in the two apical leaves of the diseased tomato was examined.

5) Protective Effect Test on Wheat Leaf Rust (WLR)

Since a plant pathogen, *Puccinia recondita*, is a parasite on living things, it was directly subcultured on wheat plant at 20±1° C. and 70% relative humidity in growth chamber. Fifteen gram of wheat seeds ('Eunpamil') were sowed in a disposable pot (diameter 6.5 cm) and grown in a greenhouse for 7 days. The wheat plants at one leaf-stage were inoculated by shaking off the pathogenic spores subcultured on wheat in a laboratory. The inoculated wheat at one leaf-stage was transferred to a dew chamber and incubated at 20° C. and 100% relative humidity to induce wheat leaf rust. Ten days after the inoculating with the spores of the wheat pathogen, a ratio of the diseased areas to total areas in the wheat leaves was examined.

6) Protective Effect Test on Barley Powdery Mildew (BPM)

Since a plant pathogen, *Erysiphe graminis* f. sp. hordei, is a parasite on living things, it was directly subcultured on barley plant at 20±1° C. and relative humidity 70% in growth chamber. Fifteen grams of barley seeds ('Dongbori No. 1') were sown in pots (diameter 6.5 cm) and grown at 25±5° C. for 7 days in a greenhouse. The leaves of barley plants at one leaf-stage were inoculated by shaking off the spores of the pathogen subcultured on leaves of barley. The inoculated barley plants were transferred to a growth chamber and incubated at 20±1° C. and 70% relative humidity for 7 days to induce barley powdery mildew. A ratio of the diseased areas to total areas of the barley leaves was examined.

Table 1 shows the results of fungicidal effect test on the above plant pathogens. The plants were treated with the fungicidal compositions one day before inoculating with the pathogens.

TABLE 1

Control efficacy of the compound of the formula 1 on the tested pathogens

| Treated compound | concentration treated (ppm) | Control value (%) | | | | | |
| --- | --- | --- | --- | --- | --- | --- | --- |
| | | RCB | RSB | CGM | TLB | WLR | BPM |
| The compound of formula 1 | 10 | 100 | 53 | 40 | 89 | 100 | 100 |
| | 2 | 100 | 21 | 30 | 79 | 99 | 98 |
| A | 50 | 90 | — | — | — | — | — |
| B | 50 | — | 50 | — | — | — | — |
| C | 40 | — | — | 40 | — | — | — |
| D | 10 | — | — | — | 80 | — | — |
| E | 10 | — | — | — | — | 85 | 85 |
| F | 10 | 98 | 5 | 10 | 57 | 93 | 94 |

A: Control fungicide (Tricylazole wettable powder)
B: Control fungicide (Validamycin soluble concentrate)
C: Control fungicide (Procymidone wettable powder)
D: Control fungicide (Dimethomotph wettable powder)
E: Control fungicide (Flusilazole wettable powder)
F: Control fungicide (Kresoxim methyl (BAS490F))

As shown in Table 1, N-methyl E-2-((2-5 methylphenyl) oxymethyl)-6-methylphenylglyoxylamide O-methyl oxime represented by the formula 1 of the present invention, showed broader and stronger fungicidal effect than the other compounds used as the conventional fungicides on several main plant pathogens. Especially, in case of barley powdery mildew and wheat leaf rust, the compound of present invention showed far superior fungicidal effect at low concentrations to a triazole-type fungicide such as flusilazole, and an acrylate-type fungicide such as kresoxim methyl (BAS490F), which have been recently developed and used. In addition, the compound of the present invention showed far stronger fungicidal effect at the very low concentration on rice blast than tricyclazole which has been extensively used until now.

Particularly, the conventional compounds were effective in protecting plants from specific pathogens, whereas the compound represented by the formula 1 of the present invention was broadly effective in protecting plants from tomato late blight, wheat leaf rust, barley powdery mildew, rice blast and rice sheath blight. Moreover, as shown in Table 1, the effective concentration of the compound of the present invention was much lower than that of the conventional compounds, so it showed excellent fungicidal effect on various plant pathogens at low concentrations.

As mentioned above, the inventors of the present invention demonstrated that N-methyl E-2-((2-methylphenyl) oxymethyl)-6-methylphenylglyoxylamide O-methyl oxime represented by formula 1 of the present invention, was very effective in protecting plants from the representative plant pathogens. To test protective effect of the compound of the present invention on other plant pathogens, the inventors performed the following experiments.

Experiment 2

Protective Effect Test II

1) Protective Effect Test on Cucumber Damping Off (CDO)

Potato (25 g) was finely ground, mixed well with overmiculite (250 mL) and autoclaved. The potato mixture was inoculated with a plant pat hogen causing cucumber damping off, Pythium ultimum, incubated at 25° C. for 15 days in a growth chamb e r and used as inoculum. Soil (150 mL) prepared by mixing vermiculite and field soil (1:1) was sterilized and mixed with the potato mixture (1 g) to use it as inoculum. After filling the inoculated soil in the pot (diameter 9 cm), five cucumber seeds (house Baekdadagio®) cucumber) were sown in the above pot and irrigated with the agricultural fungicidal compositions (10 mL) prepared at the appropriate concentrations. Seven days after the treating with the agricultural fungicidal compositions, a degree of the disease induction was examined based upon criteria for determining the disease index, and control efficacy was determined according to the above examination. The criteria was listed in the following.

Criteria

4: seeds don't germinate due to disease outbreak.

3: a young seedling dies in the middle of emergence.

2: ground surface is narrowed due to disease outbreak.

1: growth is poor due to disease outbreak of partial roots.

0: healthy plant

Control value(%)=(1-sum of the disease index in the treated plants/sum of the disease index in the untreated plants)×100

2) Protective Effect Test on Cucumber Powdery Mildew (CPM)

A plant pathogen, *Sphaerotheca fuliginea*, was prepared by collecting the diseased leaves of cucumber grown in a vinylhouse, and its spores were suspended in sterilized water. The concentration of the pathogenic spores was adjusted to $10^5$ spores/mL and used as inoculum. After a cucumber seed (house 'Baekdadagi®' cucumber) was sown in a small pot (diameter 6.5 cm), it was grown in a greenhouse for two weeks and young seedlings with the first true completely open leaf were used for test. After the young seedlings of the cucumber in the small pots were sprayed with agricultural fungicidal compositions prepared at the appropriate concentrations, they were left for 1 day in a greenhouse to dry the fungicidal compositions. The young seedlings of cucumber were inoculated with the prepared pathogenic spores of cucumber powdery mildew by spraying and incubated for 10 days in a green house to induce the disease. A ratio of the diseased areas to total areas of the first true completely open leaves was determined according to the criteria for determining a degree of disease induction.

3) Protective Effect Test on Apple Scab (APS)

A plant pathogen, *Venturia inaequalis*, was inoculated on the PDA medium. The inoculated PDA was incubated at 20° C. for 2 months in a growth chamber to form spores, and the spores were adjusted at the concentration of $2\times10^5$ spores/ml and used as inoculum. After germinating seeds of 'kukkwang' sensitive to the above pathogen at 4° C. for 3 months in refrigerator, the germinated seeds were sown in a small pot (diameter 6.5 cm), and grown for 15 days in a greenhouse to prepare young seedlings used as an apple for test. One day after the treating with agricultural fungicidal compositions, the young seedlings were inoculated with the suspension solution of spores by spraying and incubated at 20° C. and 100% relative humidity for 3 days in a dew chamber to infiltrate the plant pathogen. The young seedlings were transferred to a dew chamber at 20° C. and 70% relative humidity to induce the disease. Fifteen days after the treating with the agricultural fungicidal compositions, a ratio of the disease areas to total areas of the leaves was examined according to the standard criteria for determining a degree of disease induction, and control efficacy was calculated based upon the examination.

4) Protective Effect Test on Southern Corn Leaf Blight (CLB)

A plant pathogen, *Bipolaris maydis*, was inoculated on the Difco Lima Bean Agar (10 g/L) medium containing 10 g/L dextrose, and incubated at 24° C. with and without fluorescent light for 12 hours each time for 7 days in a growth chamber. After forming spores, the conidiospore was harvested in Tween-20 solution (250 ppm), adjusted at the concentration of $5\times10^5$ spores/ml and used as inoculum. The southern corn (golden crossbantam 70) for test was grown to be at 4 or 5-leaf stage in a greenhouse. One day after the treating with the agricultural fungicidal compositions, the inoculum was sprayed an young seedlings of the corn, and incubated at 27° C. and 100% relative humidity for 24 hours in a dew chamber to infiltrate the pathogen. The young seedling were incubated at 27° C. and 90% relative humidity for 3 days in a growth chamber to induce the disease. A ratio of diseased areas to total areas of the corn leaves was examined according to the criteria for determining a degree of disease induction.

5) Protective Effect Test on Cucumber Anthracnose (CUA)

A plant pathogen, *Colletotrichum lagenarium*, was inoculated on the PDA medium and incubated in a growth chamber at 24° C. for 7 days to form spores. The formed spore was harvested in Tween-20 solution (500 ppm), adjusted at the concentration of 10 spores/mL, and used as inoculum. The cucumber, (house 'Baekdadagi®' cucumber), in a small pot was grown to be at 2-leaf stage in a greenhouse, and tested. One day after the treating with the agricultural fungicidal compositions, the prepared inoculum (5 mL) was sprayed on leaves of the cucumber. The inoculated cucumber was incubated at 24° C. and 100% relative humidity for 1 day in a dew chamber, transferred to a growth chamber and incubated at 25–30° C. and 85% relative humidity for 7 days to induce the disease. Eight days after the inoculation, control efficacy was examined by comparing the ratio of diseased area in the second true leaves of the treated cucumber with that of the untreated cucumber.

In the above experiment 2, control value of the compound on the tested pathogens was calculated according to the following mathematical formula 1, and the results were shown in Table 2. For only cucumber damping off, it was examined according to the above-mentioned separate criteria.

Mathematical formula 1

Control value(%)=(1—the ratio of diseased area in the treated plant/the ratio of diseased area in the untreated plant)×100

TABLE 2

Control efficacy of the compound of formula 1 on the tested pathogens

| Compound | Concentration (ppm) | Control value (%) | | | | |
|---|---|---|---|---|---|---|
| | | CDO | CPM | APS | CLB | CUA |
| Chemical formula 1 | 100 | 100 | 100 | 100 | 90 | 100 |
| | 10 | 100 | 100 | 92 | 80 | 100 |
| | 1 | 30 | 80 | 60 | — | 80 |

TABLE 2-continued

Control efficacy of the compound of formula 1 on the tested pathogens

| Compound | Concentration (ppm) | CDO | CPM | APS | CLB | CUA |
|---|---|---|---|---|---|---|
| K | 10 | 20 | 85 | 85 | — | 65 |
| L | 100 | — | — | 82 | 80 | 85 |

K: Control fungicide (Benomyl, dongbuhannong chemical co., LTD thouruda ™ wettable powder)
L: Control fungicide (Mancozeb, dongbuhannong chemical co., LTD antracole ™ wettable powder)

As shown in Table 2, the acrylate-type compound of the present invention, N-methyl E-2-((2-methylphenyl)oxymethyl)-6-methylphenylglyoxylamide Q-methyl oxime, showed far superior control efficacy at low concentrations to benomyl and mancozeb, which have been used as fungicides, on cucumber damping off, cucumber powdery mildew, apple scab, southern corn leaf bliaht and cucumber anthracnose. Thus, it was demonstrated that the compound of the present invention had excellent fungicidal effect on a broad range of plant pathogens. In addition, the compound of the present invention showed superior fungicidal effect at low concentrations to conventional fungicides on various pathogens.

Experiment 3

Systemic and curative effect test
1) Systemic effect test

The following experiment was performed in order to investigate systemic effect of the acrylate-type compound represented formula 1 on several plant pathogens.

To examine the systemic effect on plant pathogens, the compound of the present invention was dissolved in acetone solution (10%), and was added with Tween-20 to be its concentration of 250 ppm. Soil in small pots which the plants were sowed, was irrigated with the above solution (10 mL) and incubated at room temperature for 24 hours to infiltrate the compound into the plant body. The above plants were inoculated with pathogens prepared as the followings. The systemic effect of the compound of the present invention was tested on rice blast, wheat leaf rust and barley powdery mildew. All the tests were repeated three times, and control values were calculated while the concentration of the compound was gradually decreased to 100 ppm, 10 ppm and 2 ppm. Tricyclazole wettable powder, flusilazole wettable powder and kresoxim methyl (BAS490F) were used as controls to compare with the compound of the present invention. The method of Experiment 1 was applied for the preparation and inoculation of pathogens, induction of diseases and examination of the control efficacy.

Control value of each compound was calculated according to the following mathematical formula 1.

Mathematical formula 1

Control value(%) (1—a ratio of the diseased areas in the treated plant/a ratio of the diseased areas in the untreated plant)

2) Curative effect test

The following experiment was performed in order to examine curative effect of the acrylate-type compound represented by the formula 1 on several plant pathogens.

To examine the curative effect on plant pathogens, plants were inoculated with each pathogen one day before the treating the compound of the present invention, and incubated in an inoculation room for 24 hours to infiltrate pathogens. The plants were sprayed with the compound of the present invention, and left at room temperature for 4 hours to volatilize solvent and water. The disease was then induced in induction room, and the curative effect was examined. The curative effect of the compound of the present invention was tested on rice blast, wheat leaf rust and barley powdery mildew. All the tests were repeated three times, and control values were calculated while the concentration of the compound was gradually decreased to 100 ppm, 10 ppm and 2 ppm). Tricyclazole wettable powder, flusilazole wettable powder and kresoxim methyl (BAS490F) were used as controls to compare with the compound of the present invention. The method of Experiment 1 was applied for the preparation and inoculation of pathogens, induction of diseases and examination of the control efficacy.

Control value was calculated according to the following mathematical formula 1.

Mathematical formula 1

Control value(%)=(1 a ratio of the diseased areas in the treated plant/a ratio of the diseased areas in the untreated plant)

Table 3 showed the systemic and curative effect on the above-mentioned plant pathogens

TABLE 3

Systemic and curative effect

| Compounds | Conc. (ppm) | RCB S.E. | RCB C.E. | WLB S.E. | WLB C.E. | BPM S.E. | BPM C.E. |
|---|---|---|---|---|---|---|---|
| Formula 1 | 100 | 56 | — | 100 | — | 100 | — |
|  | 10 | — | 84 | 100 | 100 | 80 | 100 |
|  | 2 | — | — | 43 | — | 67 | — |
| H | 100 | 0 | — | 0 | — | 29 | — |
|  | 10 | — | 39 | 0 | 0 | 8 | 50 |
|  | 2 | — | — | 0 | — | 0 | — |
| I | 100 | — | — | 11 | — | 91 | — |
|  | 10 | — | — | 0 | 97 | 17 | 81 |
|  | 2 | — | — | 0 | — | 0 | — |
| J | 100 | 87 | 0 | — | — | — | — |

H: Control fungicide (Kresoxim methyl (BAS490F))
I: Control fungicide (Flusilazole wettable powder)
J: Control fungicide (Tricyclazole wettable powder)
S.E.: Systemic effect
C.E.: Curative effect As shown in Table 3, the acrylated-type compound represented by the formula 1 of the present invention, N-methyl E-2-((2-methylphenyi oxymethyl)-6-methylphenylglyoxylamide O-methyl oxime, showed excellent systemic and curative effect when compared with the conventional fungicides, which have been widely used, on rice blast, wheat leaf rust and barley powdery mildew. Especially, in case of wheat leaf rust, the compound of the present invention showed far superior systemic and curative effect to control fungicides, and very excellent systemic and curative effect when compared with conventional fungicides such as triazole-type flusilazole or acrylate-type kesoxim methyl (BAS490F).

INDUSTRIAL APPLICABILITY

The compound of the present invention has not only stronger fungicidal effect on plant pathogens at low concentrations but also broader fungicidal spectrum than the conventional fungicides. Especially, because the compound has excellent systemic and curative effect as well as no toxicity, it can be used an efficacious agricultural fungicide. In addition, the compound of the present invention can be useful as environmental-friendly fungicide capable of causing less environmental pollution fungicide due to its strong fungicidal effect at low concentrations.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A compound of formula 1:

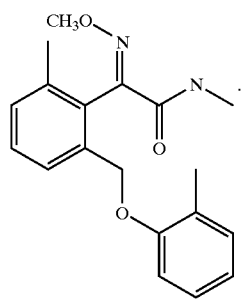

(I)

2. A method of preparing a compound of claim 1, which comprises:
   1) reacting methyl E-2-bromomethyl-6-methylphenylglyoxylate O-methyl oxime with o-cresol in the presence ofa base to form methyl E-2-((2-methylphenyl)oxymethyl)-6-methylphenylglyoxylate O-methyl oxime; and,
   2) reacting the methyl E-2-((2-methylphenyl)oxymethyl)-6-methylphenylglyoxylate O-methyl oxime prepared in step 1 with methylamine to form N-methyl E-2-((2-methylphenyl)oxymethyl)-6-methylphenylglyoxylamide O-methyl oxime.

3. The method according to claim 2, wherein the reacting of methyl E-2-((2-methylphenyl)oxymethyl)-6-methylphenylglyoxylate O-methyl oxime with methylamine is carried out in the presence of a solvent.

4. The method according to claim 2, wherein the number of equivalents of methylamine used is 1–10.

5. The method according to claim 2, wherein the reaction temperature of the reacting of the of methyl E-2-((2-methylphenyl)oxymethyl)-6-methylphenylglyoxylate O-methyl oxime with methylamine is 0–100° C.

6. A fungicidal composition comprising a n effective amount of the compound of claim 1.

7. A method of protecting plants from the foliar and soilborne diseases of crops, fruits, vegetables, grass and flowers, comprising applying an effective amount of the fungicidal composition of claim 6 to said plants.

8. The method according to claim 7, wherein the diseases are selected from the group consisting of barley powdery mildew, wheat leaf rust, rice blast, rice sheath blight, cucumber gray mould, tomato late blight, cucumber damping off, cucumber powdery mildew, apple scab, southern corn leaf blight and cucumber anthracnose.

9. The method according to claim 6, further comprising applying to a member of the group consisting of fungicides, insecticides, herbicides, plant growth regulators and fertilizers.

10. The method of claim 2, wherein the base is selected from the group comprising $K_2CO_3$, $Na_2CO_3$, triethylamine and sodium hydride.

11. The method of claim 3, wherein the solvent is selected from the group comprising dimethyl formamide, dimethyl sulfoxide, tetrahydrofuran, chloroform, methylene chloride, ethylene dichloride, benzene, toluene, xylene, methanol, ethanol, isopropanol, hexane, pentane, diethyl ether and 1,4-dioxane.

12. The method of claim 4, wherein the number of equivalents of methylamine used is 5.

13. The method of claim 5, wherein the reaction temperature of the reaction of the of methyl E-2-((2-methylphenyl)oxymethyl)-6-methylphenylglyoxylate O-methyl oxime with methylamine is 0–30° C.

14. A method of protecting seeds and agricultural products during storage, comprising applying an effective amount of the fungicidal composition of claim 6 to said seeds and agricultural products.

* * * * *